US006851427B1

(12) United States Patent
Nashed

(10) Patent No.: US 6,851,427 B1
(45) Date of Patent: Feb. 8, 2005

(54) BREATHING CIRCUIT DISCONNECT WARNING SYSTEM AND METHOD FOR USING A DISCONNECT SYSTEM

(76) Inventor: Ramses Nashed, 626 Boca Ciega Isle Dr., St. Pete Beach, FL (US) 33706

( * ) Notice: Subject to any disclaimer, the term of this patent is extended or adjusted under 35 U.S.C. 154(b) by 0 days.

(21) Appl. No.: 10/463,888

(22) Filed: Jun. 18, 2003

Related U.S. Application Data

(63) Continuation-in-part of application No. 10/428,480, filed on May 2, 2003.

(51) Int. Cl.[7] .................................................. A62B 7/00
(52) U.S. Cl. ............................ 128/205.23; 128/204.18; 128/207.14
(58) Field of Search ....................... 128/200.24, 204.18, 128/205.23, 207.14–207.18, 203.12, 202.27; 600/529–543; 333/24 R; 285/47; 439/1, 23, 207, 28–33, 208; 307/89, 119

(56) References Cited

U.S. PATENT DOCUMENTS

| | | | | | |
|---|---|---|---|---|---|
| 3,654,915 A | * | 4/1972 | Sanctuary | .................... | 600/495 |
| 3,796,197 A | * | 3/1974 | Locher et al. | ............... | 123/357 |
| 4,796,615 A | * | 1/1989 | Bullock et al. | ......... | 128/202.27 |
| 5,555,890 A | * | 9/1996 | Schaller | ....................... | 600/532 |
| 6,098,617 A | * | 8/2000 | Connell | .................. | 128/200.26 |
| 6,575,165 B1 | * | 6/2003 | Cook et al. | ............. | 128/206.17 |
| 6,632,402 B2 | * | 10/2003 | Blazewicz et al. | ............. | 422/84 |
| 6,656,127 B1 | * | 12/2003 | Ben-Oren et al. | ........... | 600/532 |
| 2001/0017134 A1 | * | 8/2001 | Bahr | ...................... | 128/204.18 |
| 2003/0105407 A1 | * | 6/2003 | Pearce et al. | ................ | 600/532 |

* cited by examiner

Primary Examiner—Glenn K. Dawson
(74) Attorney, Agent, or Firm—Edward P. Dutkiewicz

(57) ABSTRACT

A breathing circuit disconnect warning system comprising an endotracheal tube, a breathing circuit supply tube with a pair of spaced electrically conductive strips, and a coupling tube. The coupling tube has an output end with a normally open switch including a first electrically conductive element and a spaced second electrically conductive element. The coupling tube also has an input end with a first electrically conductive ring and a second electrically conductive ring and lines coupling the rings and the elements. The rings are positionable in contact with the strips of the supply tube, whereby upon inserting the endotrachial tube into the output end, the switch will close and there will be an electrical connection across the switch and lines and rings and strips.

6 Claims, 6 Drawing Sheets

BREATHING CIRCUIT DISCONNECT WARNING SYSTEM AND METHOD FOR USING A DISCONNECT SYSTEM

RELATED APPLICATION

The present application is a continuation-in-part application of U.S. patent application Ser. No. 10/428,480 filed May 2, 2003.

BACKGROUND OF THE INVENTION

1. Field of the Invention

The present invention relates to a breathing circuit disconnect warning system and a method for using a disconnect system and more particularly pertains to allowing a user to monitor continuity within a breathing circuit.

2. Description of the Prior Art

The use of disconnect warning systems of known designs and configurations is known in the prior art. More specifically, disconnect warning systems of known designs and configurations previously devised and utilized for the purpose of warning a user of a disconnect through conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,796,197 issued Mar. 12, 1974, to Locher et al discloses an electronic regulator with fuel injection control for diesel engines. U.S. Pat. No. 3,654,915 issued Apr. 11, 1972 to Sanctuary discloses an apparatus for automatically measuring and indicating blood pressure. U.S. Pat. No. 6,098,617 issued Aug. 8, 2000, to Connell discloses a device for administering/sampling inhalant/expired gases in an oro/nasopharyngeal airway. Lastly, U.S. Pat. No. 5,555,890 issued Sep. 17, 1996, discloses a pharyngeal end-tidal carbon dioxide measuring catheter.

While these devices fulfill their respective, particular objectives and requirements, the aforementioned patents do not describe a breathing circuit disconnect warning system and a method for using a disconnect system that allows allowing a user to monitor continuity within a breathing circuit.

In this respect, the breathing circuit disconnect warning system and a method for using a disconnect system according to the present invention substantially departs from the conventional concepts and designs of the prior art, and in doing so provides an apparatus and a method primarily developed for the purpose of allowing the user to monitor continuity within a breathing circuit.

Therefore, it can be appreciated that there exists a continuing need for a new and improved breathing circuit disconnect warning system and a method for using a disconnect system which can be readily used for allowing the user to monitor continuity within the breathing circuit. In this regard, the present apparatus and method substantially fulfills this and various needs.

SUMMARY OF THE INVENTION

In view of the disadvantages inherent in the known types of disconnect warning systems of known designs and configurations now present in the prior art, the present invention provides an improved breathing circuit disconnect warning system and a method for using a disconnect system. As such, the general purpose of the present invention, which will be described subsequently in greater detail, is to provide a new and improved breathing circuit disconnect warning system and a method for using a disconnect system which has all the advantages of the prior art and none of the disadvantages.

To attain this, the present invention essentially comprises a breathing circuit disconnect warning system connector for monitoring continuity within a breathing circuit. The system comprises, in combination, an endotracheal tube having a tubular portion fabricated of flexible non-conductive material and a coupling portion with a leading edge, the coupling portion and leading edge being generally rigid in a cylindrical configuration with a first axis and having an exterior surface with a first exterior diameter.

The system also comprises a breathing circuit connector functioning as a supply tube fabricated of an essentially rigid electrically non-conductive material having a tubular portion and a coupling portion with a leading edge, the coupling portion and leading edge being generally rigid in a cylindrical configuration with a second axis and having an interior surface with a first interior diameter, the interior surface of the coupling portion having a pair of spaced parallel electrically conductive strips extending around the entire circumference of the interior surface and adapted to be electrically coupled to a first circuit for detecting continuity of the first circuit.

Lastly, the system also comprises an elbow functioning as a coupling tube fabricated of an essentially rigid electrically non-conductive material and having an output end in a cylindrical configuration with an axis positionable coextensive with the first axis of the endotrachial tube and having an interior surface with an interior diameter slightly greater than the exterior diameter of the endotrachial tube.

The interior surface adjacent to the input end has a first electrically conductive element and a spaced second electrically conductive element and an adjacent electrically conductive finger. The finger is formed with a fixed end pivotally coupled to the coupling tube and a free end resiliently biased away from the second electrically conductive element. The free end is positioned adjacent to the second electrically conductive element.

The coupling tube also has an output end in a cylindrical configuration with an axis positionable coextensive with the axis of the supply tube perpendicular to the first axis of the endotrachial tube and also has an exterior surface with an exterior diameter slightly less than the interior diameter of the supply tube. The exterior surface adjacent to the input end has a first electrically conductive ring and a second electrically conductive ring positionable in contact with the a pair of spaced parallel electrically conductive strips of the supply tube. The electrically conductive elements and the finger constitute a switch. Electrical lines couple the electrically conductive elements and the electrically conductive rings such that when the input end of the coupling tube is inserted into the supply tube and the endotracheal tube is inserted into the output end of the coupling tube, the switch will become closed and there is an electrical connection across the finger and between the electrically conductive elements and electrical lines and rings and strips.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved breathing circuit disconnect warning system and a method for using a disconnect system which has all of the advantages of the prior art disconnect warning systems of known designs and configurations and none of the disadvantages.

It is another object of the present invention to provide a new and improved breathing circuit disconnect warning system and a method for using a disconnect system which may be easily and efficiently manufactured and marketed.

It is further an object of the present invention to provide a new and improved breathing circuit disconnect warning system and a method for using a disconnect system which is of durable and reliable constructions.

An even further object of the present invention is to provide a new and improved breathing circuit disconnect warning system and a method for using a disconnect system which is susceptible of a low cost of manufacture with regard to both materials and labor, and which accordingly is then susceptible of low prices of sale to the consuming public, thereby making such breathing circuit disconnect warning system and a method for using a disconnect system economically available to the buying public.

Even still another object of the present invention is to provide a breathing circuit disconnect warning system and a method for using a disconnect system for allowing a user to monitor continuity within a breathing circuit thereby increasing patient safety.

Lastly, it is an object of the present invention to provide a new and improved breathing circuit disconnect warning system and a method. The system, as described herein comprises an endotracheal tube; a breathing circuit supply tube with a pair of spaced electrically conductive strips; and a coupling tube. The coupling tube has an output end with a normally open switch including a first electrically conductive element and a spaced second electrically conductive element. The coupling tube also has an input end with a first electrically conductive ring and a second electrically conductive ring and lines coupling the rings and the elements. The rings are positionable in contact with the strips of the supply tube, whereby upon inserting the endotrachial tube into the output end, the switch will close and there will be an electrical connection across the switch and lines and rings and strips.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
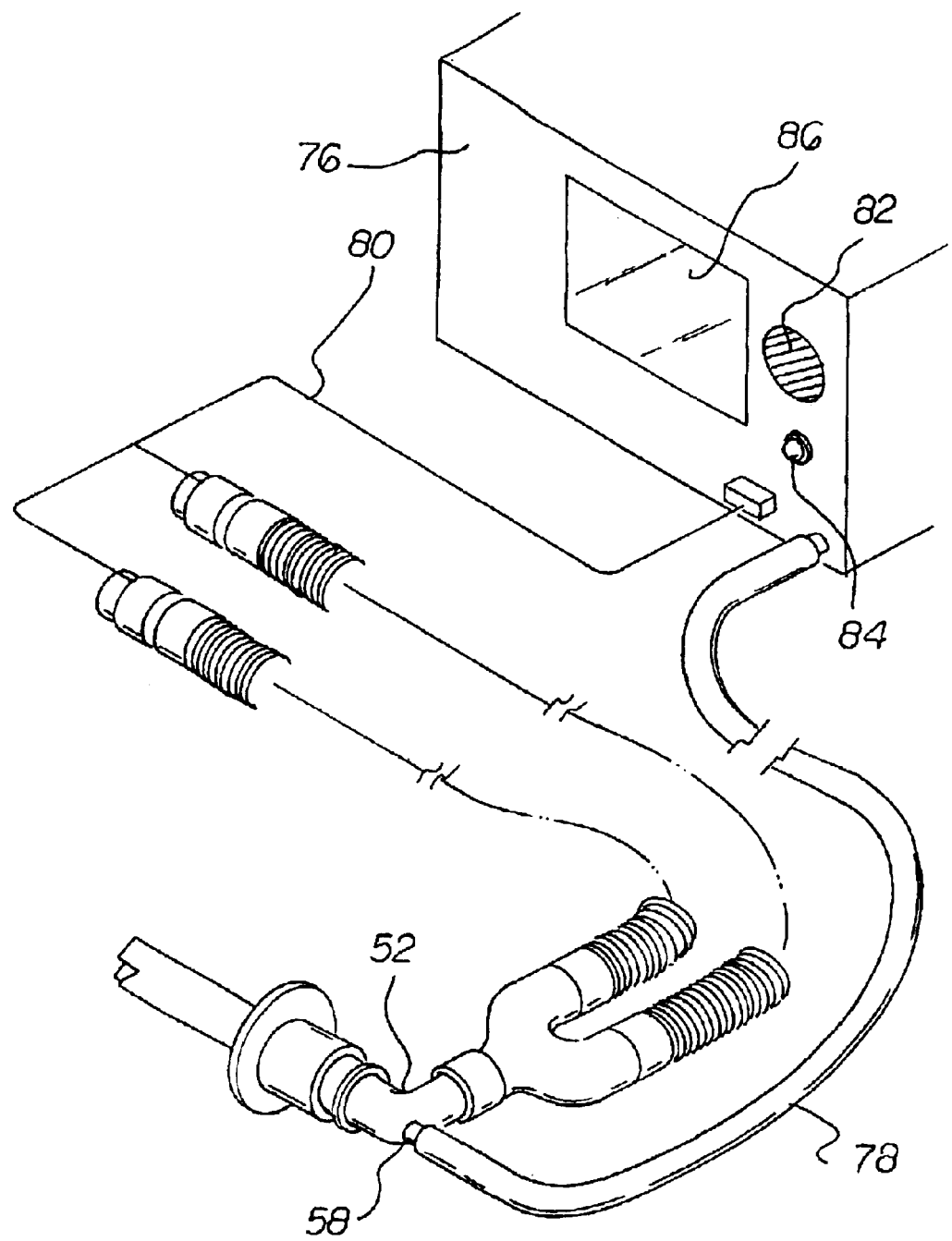
FIG. 1 is a perspective illustration of the breathing circuit disconnect warning system constructed in accordance with the principles of the present invention.
Figure 2:
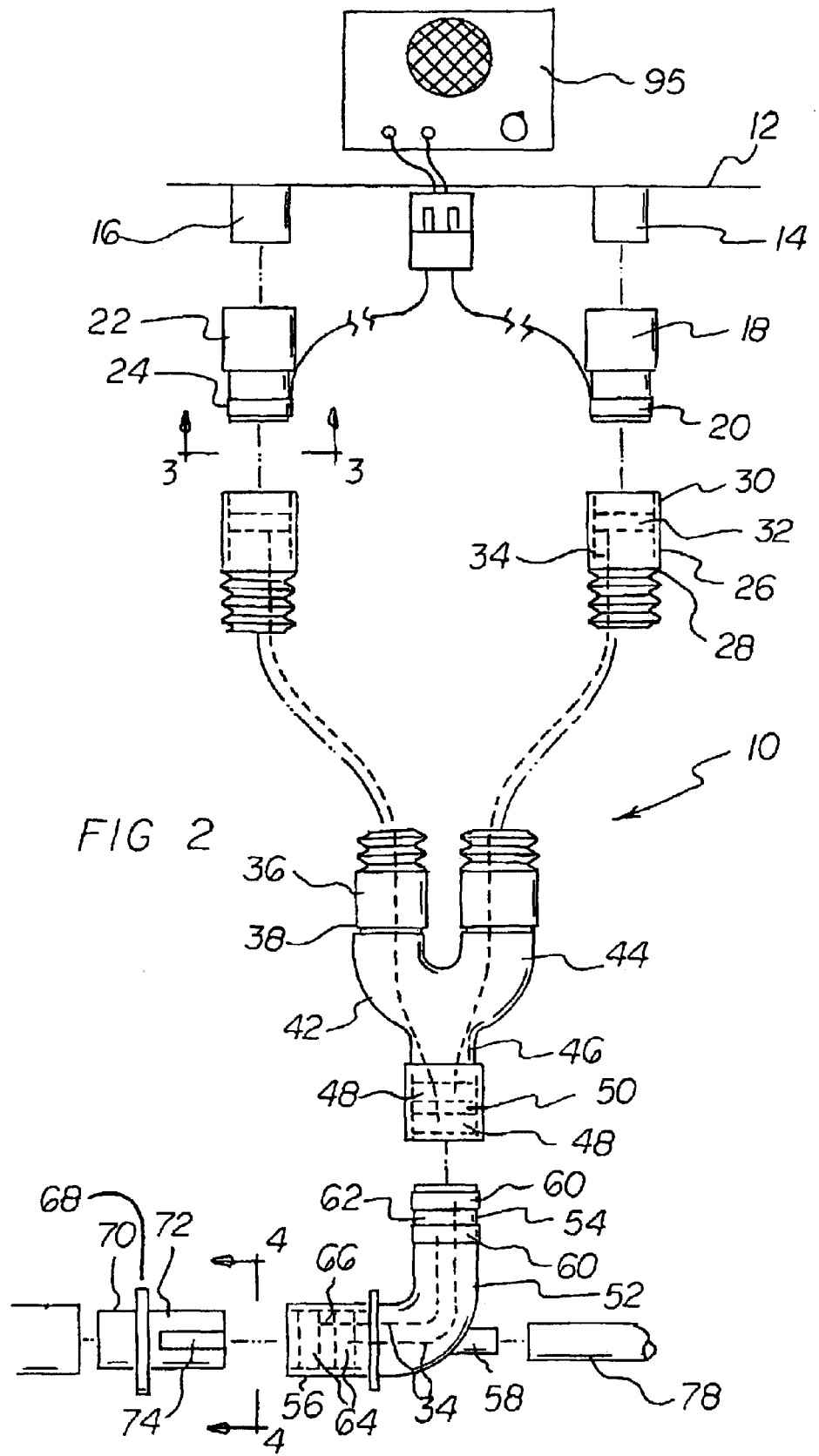
FIG. 2 is a plan view of the present invention shown in an exploded fashion.
Figure 2A:
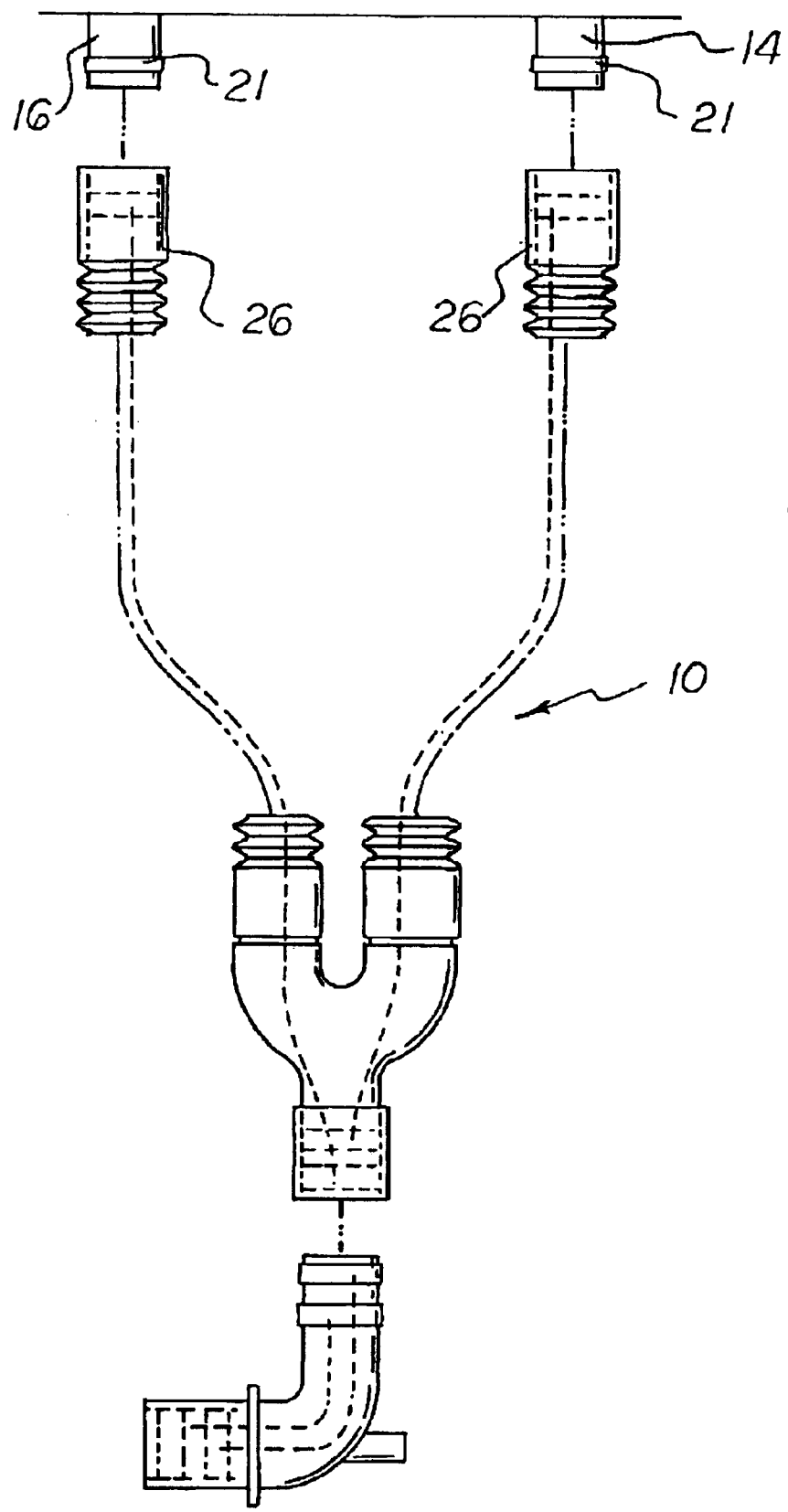
Figures 3, 4, 5:
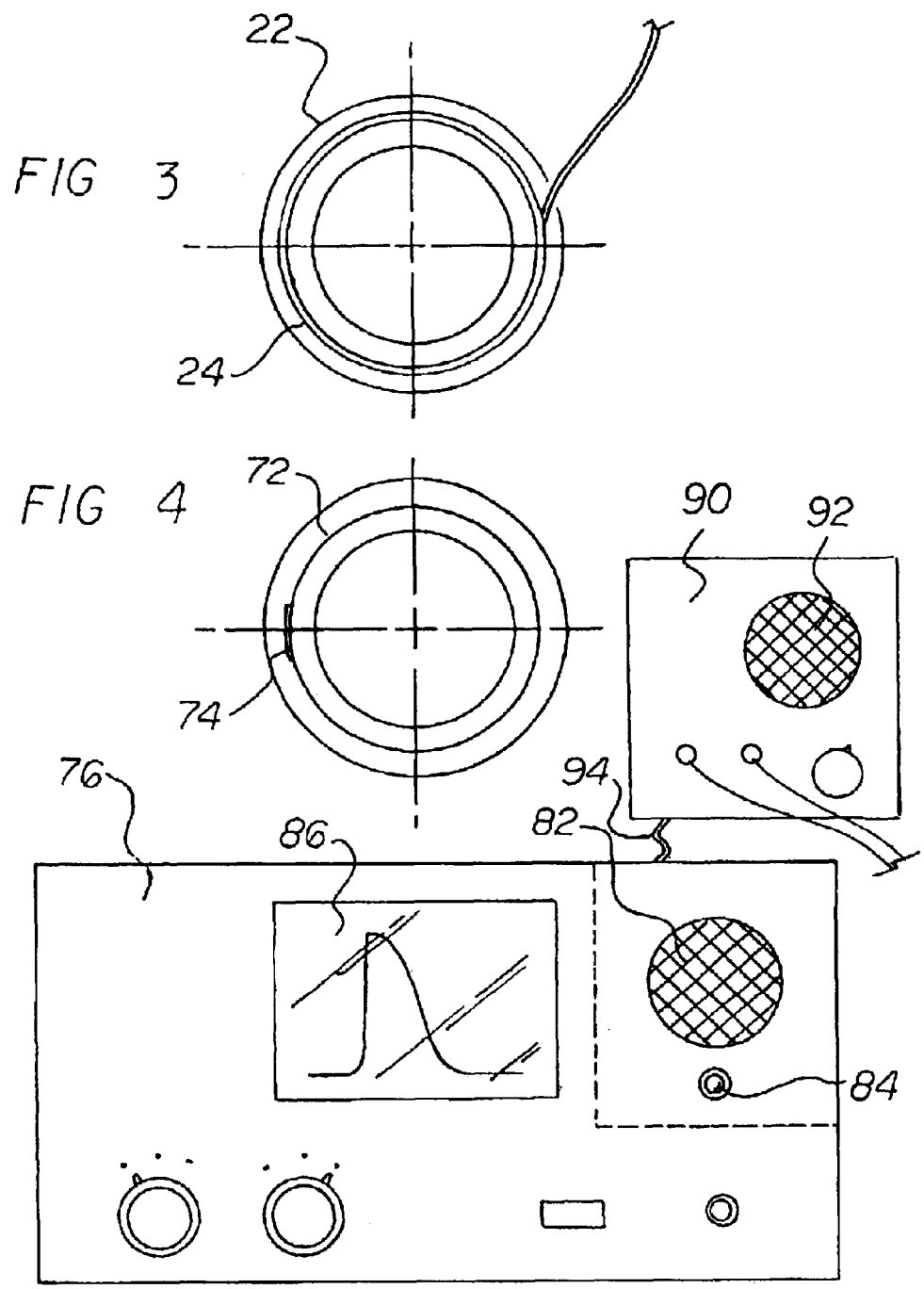
FIG. 3 is an end view of the inward coupling end piece taken along line 3—3 of FIG. 2.
FIG. 4 is also an end view of the coupling portion of the endotracheal tube connector taken along line 4—4 of FIG. 2.
FIG. 5 is a front view of the capnograph.

With reference now to the drawings, and in particular to FIG. 1 thereof, the preferred embodiment of the new and improved breathing circuit disconnect warning system and a method for using a disconnect system embodying the principles and concepts of the present invention and generally designated by the reference numeral 10 will be described.

The present invention, the breathing circuit disconnect warning system and a method for using a disconnect system 10 is comprised of a plurality of components. Such components in their broadest context include a gas circuit, a plurality of circuit adapters, an anesthesia breathing circuit, and an endotracheal tube. Such components are individually configured and correlated with respect to each other so as to attain the desired objective.

First provided is a gas circuit 12. The gas circuit has an outlet 14 with a first outer diameter. The gas circuit also has an inlet 16 with a first outer diameter.

A first gas circuit outlet adapter 18 is provided. The first gas circuit outlet adapter has a generally round tubular configuration. The first gas circuit outlet adapter has an inward end and an outward end. The inward end has a first inner diameter. The first inner diameter is mated to the first outer diameter of the gas circuit outlet. In this manner the coupling of the adapter to the gas circuit outlet first outer diameter is allowed. The first gas circuit outlet adapter has an outer end outer diameter. The outer end outer diameter is the same size as the gas circuit outlet outer diameter. The first adapter outlet has an electronic coupling collar 20. The collar is located on the outer diameter of the adapter outlet. The collar is electronically coupled to a first wire.

Next provided is a second gas circuit inlet adapter 22. The second gas circuit inlet adapter has a generally round tubular configuration. The second gas circuit inlet adapter has an inward end and an outward end. The inward end has a first inner diameter. The first inner diameter is mated to the first outer diameter of the gas circuit inlet. In this manner the coupling of the adapter to the gas circuit inlet is allowed. The second gas circuit inlet adapter has an outer end outer diameter. The outer end outer diameter is the same size as the gas circuit inlet outer diameter. The first adapter outlet has an electronic coupling collar 24. The collar is located on the outer diameter of the adapter outlet. The collar is electronically coupled to a second wire.

In an alternative embodiment, the gas circuit outlet and inlet of an anesthesia machine would have a external conductive band 21 about the periphery, that band being coupled to an internal circuit continuity monitor of an anesthesia machine.

An anesthesia breathing circuit subassembly is provided next. The subassembly is fabricated of a flexible material. The subassembly has a pair of tubular circuit breathing hoses. The breathing hoses have a third internal diameter. The breathing hoses have a Y connector and a connecting elbow. Each of the breathing hoses has an outward end and an inward end. A length is provided between the outward and inward ends. The inward end of each hose has an inward coupling end piece 26. The end piece has an outer end 28 and an inner end 30. Each inward end of the end piece has a first internal diameter sized to couple with the first outer diameter of the outer adapter. The end piece of each of the breathing hoses has an electrically conductive collar 32. The collar is within the inner diameter of the inner end piece. In this manner the end piece mates with and forms an electronically conductive connection with the conductive collar of the gas circuit outlet adapter. The end piece collar has an electronically conductive means 34, such as a wire. The electronically conductive means is coupled to the end piece collar. The conductive means passes outwardly within the inner diameter of the length of the breathing hose. Each of the outward ends of the breathing hoses have an outward coupling end piece 36. The outward coupling end piece has an inner end and an outer end 38. The outer end of the outward coupling end piece has a first internal diameter. The inner end of the outward coupling end piece has a third external diameter. Each outer end piece has an electronically conductive means passing from within the length of the breathing hose outwardly through to the outward most end of the outward end piece. The inner end of the outward end piece is coupled to the outermost end of the breathing hose.

The Y connector 42 has a generally hollow tubular Y shaped configuration. The Y connector has two inward bifurcated portions 44. The Y connector has an outward common portion 46. Each of the bifurcated portions has a first external diameter and is sized to be accepted into the internal diameter of the outer end of the outward end piece of each of the hoses. The electronically conductive means passes through the internal diameter of the Y connector toward the outward common end. The outward common end of the Y piece has a single hollow tubular configuration. The outward common end of the Y piece has a second internal diameter. The outward common end has a pair of conductive collars 48. The collars are located within the second internal diameter. The collars are circumferentially parallel with a non-conductive space 50 between the collars. Each of the electronically conductive means is coupled to one of the collars in the common end of the Y piece.

The elbow 52 has a generally hollow tubular configuration. The elbow has an inward portion 54 and an outward portion 56. A capnograph connection port 58 is provided between the inward and outward portions. The inward portion has a second external diameter. The outward portion has a second internal diameter. The inward portion has a pair of conductive collars 60. The collars are located on the external surface of the second external diameter. The collars are circumferentially parallel with a non-conductive space 62 between the collars. The second internal diameter of the outward portion of the elbow has a pair of conductive collars 64. The collars are located within the second internal diameter. The collars are circumferentially parallel with a non-conductive space 66 between the collars. A conductive means 34 electronically couples the inward collar of the outward portion and the inward collar of the inward portion. A conductive means electronically couples the outward collar of the outward portion and the outward collar of the inward portion.

Provided next is an endotracheal tube connector 68. The endotracheal tube connector is fabricated of flexible non-conductive material. The endotracheal tube connector has a tubular portion 70 and a coupling portion 72. The coupling portion has a generally hollow tubular configuration. The coupling portion has a second external diameter. The tubular portion has a third external diameter. The external diameter of the coupling portion has a conductive strip 74. The conductive strip is aligned in an inward to outward direction. In this manner the conductive collars of the outward portion of the elbow are electronically coupled when the endotracheal tube connector is pushed into the second internal diameter of the elbow.

Provided last is a capnograph 76. The capnograph has a sampling tube 78. The sampling tube is coupled to the connection port of the elbow. The capnograph also has a pair of wires 80 coupling the capnograph to the circuit adapters. The capnograph also has a program which then initiates an adjustable timer when the endotracheal connector completes the circuit by connecting the collars of the outward elbow with the conductive strip. The timer provides the transmission of an alarm 82 when the circuit had been completed and no carbon dioxide is detected in the breathing hoses within a predetermined amount of time. The program also provides the transmission of a second alarm 84 if carbon dioxide was detected in the anesthesia circuit and the parallel monitoring circuits were not connected by the strip in the endotracheal tube. The second alarm is capable of being turned off. The program also provides a third alarm 86 if the circuit is interrupted once it is connected and made continuous by the endotracheal tube conductive strip.

In an alternate embodiment of the present invention a stand-alone programable circuit monitor 90 is also included. The monitor may be coupled electronically 94 to a capnograph or may be a stand alone circuit monitor 95. The capnograph sends a signal to the stand-alone circuit monitor when the presence of carbon dioxide is detected. The stand-alone circuit monitor determines if alarm criteria is attained and transits an alarm 92 if the criteria is attained.

In the alternative embodiment with a stand-alone monitor, the monitor would not be coupled with the capnograph, but would only monitor circuit continuity.

The present intention also comprises a method for using a disconnect system and thereby allowing a user to monitor continuity within a breathing circuit comprising.

The first step of the method is providing an anesthesia breathing circuit having an electrically conductive coupling between each of the components thereby forming a plurality of unconnected electrical circuits. The anesthesia breathing circuit is coupled electronically to the anesthesia machine having a inlet and an outlet.

The next step is providing an endotracheal tube having a conductive strip thereby allowing a user to connect the unconnected circuits and form a single continuous electrical circuit when the user connects the endotracheal tube to the breathing circuit elbow.

The next step is providing a capnographer having a sampling tube coupled to the breathing circuit, the capnographer also having a pair of wires electrically coupling the capnographer to the electrical circuit, the capnographer also having program which would begin an adjustable timer when the coupling of an endotracheal with the breathing circuit completed the electrical circuit by connecting the collars of the outward elbow with the conductive strip of the endotracheal tube, said timer providing the transmission of an alarm when the circuit had been completed and no carbon dioxide was detected in the breathing hoses within a predetermined amount of time and said timer also providing the transmission of an alarm when the circuit is connected and then disconnected and said timer providing an alarm if carbon dioxide was detected and the electrical circuit was not coupled to a continuous circuit.

The last step is forming a continuous electrical circuit monitoring system which triggers an alarm if the circuit is electrically disconnected and triggers an alarm if the presence of carbon dioxide is not detected within the breathing circuit within a pre-set time and triggers an alarm if carbon dioxide is detected and the electrical circuit is not formed into a continuous circuit, allowing a user to monitor anesthesia circuit continuity and to detect interruptions of the breathing circuit.

An alternative embodiment of the above method would be providing a stand-alone monitor, not coupled with a capnograph, to monitor the continuity of an anesthesia circuit.

Additional alternate embodiments of the invention are illustrated in FIGS. 6 through 9. In the alternate embodiment of FIG. 6, there is disclosed a breathing circuit disconnect warning system 100 connector for monitoring continuity within a breathing circuit. Such system comprises, in combination, an endotracheal tube 104 having a tubular portion 106. The endotrachial tube is fabricated of flexible non-conductive material and has a coupling portion 108 with a leading edge 110. The coupling portion and leading edge are generally rigid in a cylindrical configuration with a first axis and have an exterior surface with a first exterior diameter.

Next provided is a breathing circuit connector functioning as a supply tube 114. The supply tube is fabricated of an essentially rigid electrically non-conductive material and has a tubular portion 116 and a coupling portion 118 with a leading edge 120. The coupling portion and leading edge are generally rigid in a cylindrical configuration with a second axis and having an interior surface with a first interior diameter. The interior surface of the coupling portion has a pair of spaced parallel electrically conductive strips 122, 124 extending around the entire circumference of the interior surface. The strips are adapted to be electrically coupled to a first circuit for detecting continuity of the first circuit.

Lastly provided is an elbow functioning as a coupling tube 128. The coupling tube is fabricated of an essentially rigid electrically non-conductive material. The coupling tube has an output end 130 in a cylindrical configuration with an axis positionable coextensive with the first axis of the endotrachial tube. The coupling tube also has an interior surface with an interior diameter slightly greater than the exterior diameter of the endotrachial tube. The interior surface adjacent to the input end has a first electrically conductive element 132 and a spaced second electrically conductive element 134 and an adjacent electrically conductive finger 136. The finger is formed with a fixed end 138 pivotally coupled to the coupling tube and a free end 140 resiliently biased away from the second electrically conductive element. The free end is positioned adjacent to the second electrically conductive element.

The coupling tube also has an output end 142 in a cylindrical configuration with an axis positionable coextensive with the axis of the supply tube perpendicular to the first axis of the endotrachial tube. The output end also has an exterior surface with an exterior diameter slightly less than the interior diameter of the supply tube. The exterior surface adjacent to the input end has a first electrically conductive ring 144 and a second electrically conductive ring 146 positionable in contact with the a pair of spaced parallel electrically conductive strips of the supply tube. The electrically conductive elements and the finger constitute a switch with electrical lines 148, 150 coupling the electrically conductive elements and the electrically conductive rings such that when the input end of the coupling tube is inserted into the supply tube and the endotracheal tube is inserted into the output end of the coupling tube, the switch will become closed and there is then created an electrical connection across the finger and between the electrically conductive elements and electrical lines and rings and strips.

Figure 6:
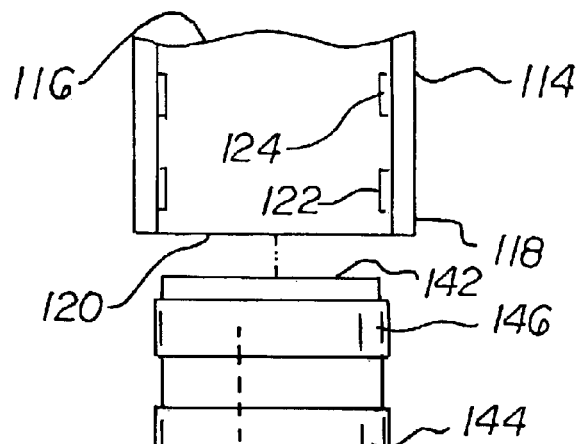
FIG. 6 is a front elevational view of a coupling tube and endotrachial tube and supply tube constructed in accordance with an alternate embodiment of the invention.
Figure 6:
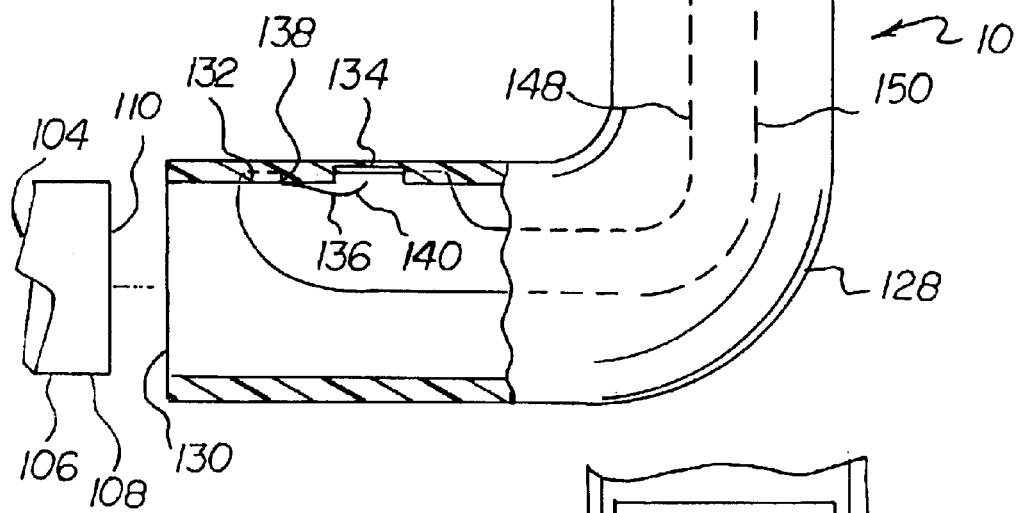
Figure 7:
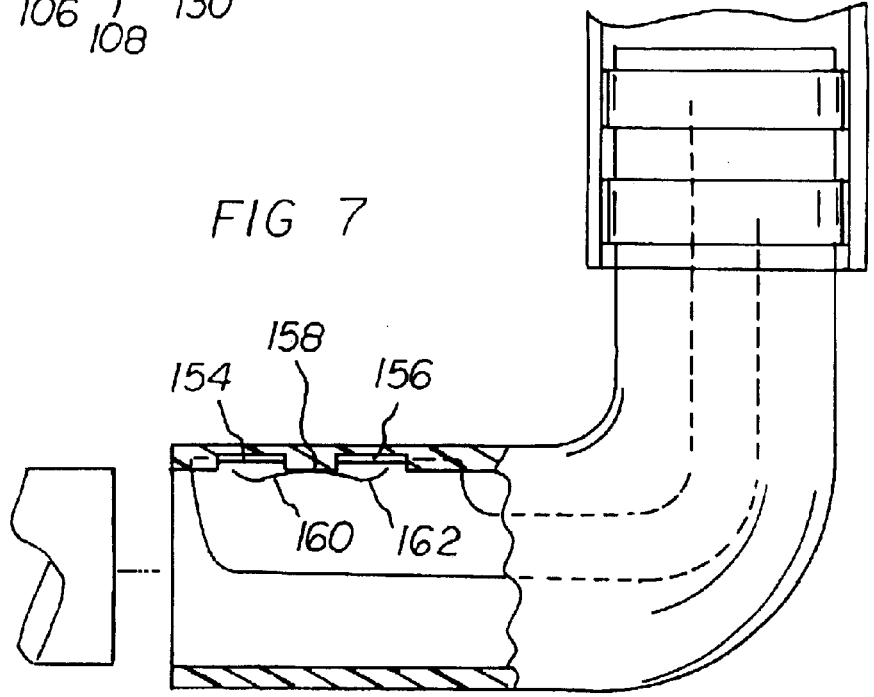
FIG. 7 is a front elevational view of a coupling tube and endotrachial tube and supply tube constructed in accordance with another alternate embodiment of the invention.

In the FIG. 7 embodiment, all of the components of the system are the same as in the FIG. 6 embodiment except for the switch. The switch of the FIG. 7 embodiment includes two spaced electrical elements 154, 156 and an electrically conductive finger. The finger has a fixed central extend 158 end and two free ends 160, 162. The free ends are movable into contact with the elements to close the switch and a circuit.

Figure 8:
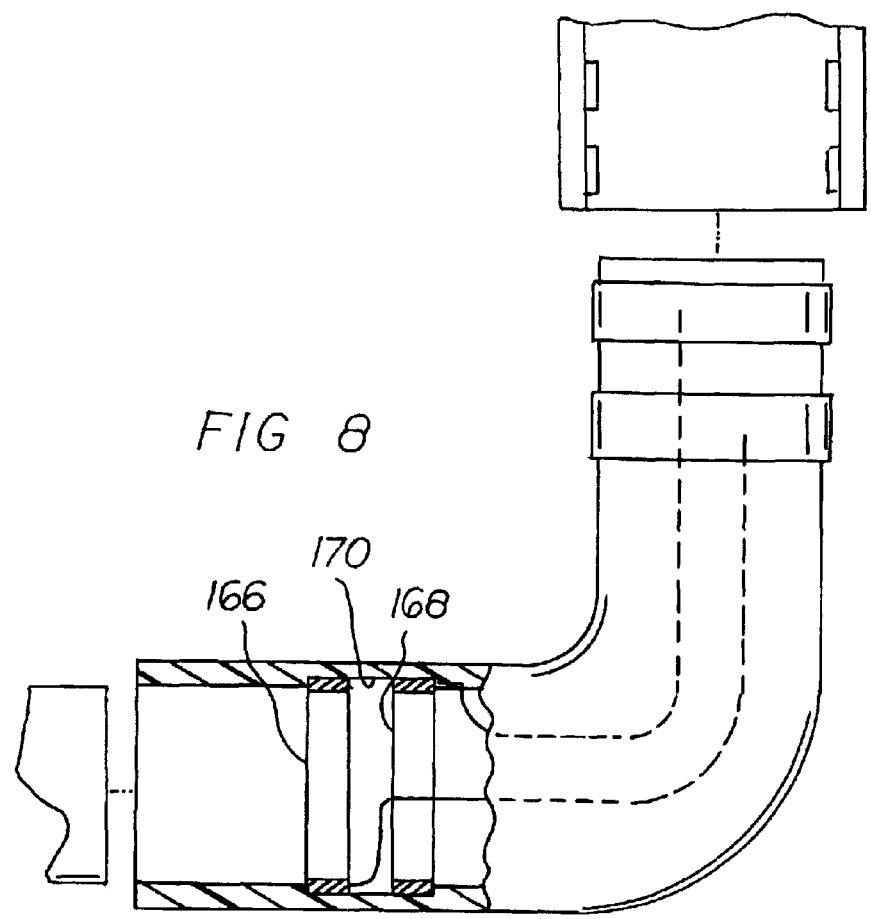
FIGS. 8 and 9 are front elevational views, partly in cross section, of a coupling tube and endotrachial tube and supply tube constructed in accordance with a final alternate embodiment of the invention.
Figure 9:
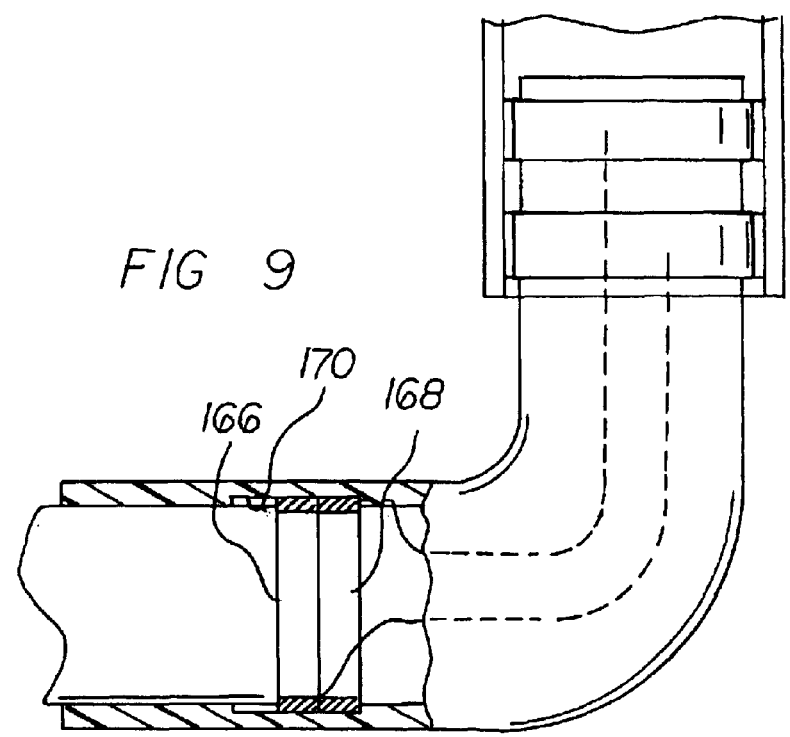

In the final embodiment, all of the components of the system are the same as in the FIGS. 6 and 7 embodiments except for the switch. FIG. 8 illustrates the switch in the open orientation while FIG. 9 illustrates the switch in the closed orientation. The switch of this embodiment includes a first and a second spaced electrical elements 166, 168. The elements each have a cylindrical configuration. The first elements 168 is fixedly positioned in the interior surface of the coupling tube. The second element 166 is axially slidable in the interior surface of the coupling tube. A groove 170 receives the second element whereby when the endotrachial tube is inserted into the input end of the coupling tube it will slide the second element within the groove into contact with the first element to close the switch and a circuit.

The present invention also includes the method of using the breathing circuit disconnect warning system as described above. Such method comprises the steps of first providing an endotracheal tube. The next step is providing a breathing circuit supply tube with a pair of spaced electrically conductive strips. The next step is providing a coupling tube having an output end with a normally open switch including a first electrically conductive element and a spaced second electrically conductive element, the coupling tube also having an input end with a first electrically conductive ring and a second electrically conductive ring and lines coupling the rings and the elements. The method further includes the step of inserting the input end of the coupling tube into the supply tube to bring the rings of the coupling tube into contact with the strips of the supply tube. The method lastly includes the step of inserting the endotrachial tube into the output end coupling tube whereby the switch will close and there will be an electrical connection across the switch and lines and rings and strips.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A breathing circuit disconnect warning system connector for monitoring continuity within a breathing circuit comprising, in combination:

an endotracheal tube having a tubular portion fabricated of flexible non-conductive material and a coupling portion with a leading edge, the coupling portion and leading edge being generally rigid in a cylindrical configuration with a first axis and having an exterior surface with a first exterior diameter;

a breathing circuit connector functioning as a supply tube fabricated of an essentially rigid electrically non-conductive material having a tubular portion and a coupling portion with a leading edge, the coupling portion and leading edge being generally rigid in a cylindrical configuration with a second axis and having an interior surface with a first interior diameter, the interior surface of the coupling portion having a pair of spaced parallel electrically conductive strips extending around the entire circumference of the interior surface and adapted to be electrically coupled to a first circuit for detecting continuity of the first circuit; and an elbow functioning as a coupling tube fabricated of an essentially rigid electrically non-conductive material and having an output end in a cylindrical configuration with an axis positionable coextensive with the first axis of the endotracheal tube and having an interior surface with an interior diameter slightly greater than the exterior diameter of the endotracheal tube, the elbow also having an input end, with the interior surface of the elbow adjacent to the input end having a first electrically conductive element and a spaced second electrically conductive element and an adjacent electrically conductive finger, the finger formed with a fixed end pivotally coupled to the coupling tube and a free end resiliently biased away from the second electrically conductive element, the free end being positioned adjacent to the second electrically conductive element, the coupling tube also having an output end in a cylindrical configuration with an axis positionable coextensive with the axis of the supply tube perpendicular to the first axis of the endotrachial tube and having an exterior surface with an exterior diameter slightly less than the interior diameter of the supply tube, the exterior surface adjacent to the input end having a first electrically conductive ring and a second electrically conductive ring positionable in contact with the pair of spaced parallel electrically conductive strips of the supply tube, the electrically conductive elements and the finger constituting a switch, and electrical lines coupling the electrically conductive elements and the electrically conductive rings such that when the input end of the coupling tube is inserted into the supply tube and the endotracheal tube is inserted into the output end of the coupling tube, the switch will become closed and there is an electrical connection across the finger and between the electrically conductive elements and electrical lines and rings and strips.

2. A breathing circuit disconnect warning system comprising:

an endotracheal tube;

a breathing circuit supply tube with a pair of spaced electrically conductive strips; and a coupling tube having an output end with a normally open switch including a first electrically conductive element and a spaced second electrically conductive element, the coupling tube also having an input end with a first electrically conductive ring and a second electrically conductive ring and lines coupling the rings and the elements, the rings being positionable in contact with the strips of the supply tube, whereby upon inserting the endotracheal tube into the output end, the switch will close and there will be an electrical connection across the switch and lines and rings and strips.

3. The system as set forth in claim 2 wherein the switch includes two spaced electrical elements and an electrically conductive finger, the finger having a fixed end and a free end, the free end being movable into contact with one of the elements to close the switch and a form a circuit.

4. The system as set forth in claim 2 wherein the switch includes two spaced electrical elements and an electrically conductive finger, the electrically conductive finger having a fixed central extend end and two free ends with the free ends being movable into contact with the spaced electrical elements to close the switch and a form circuit.

5. The system as set forth in claim 2 wherein the switch includes a first and a second spaced electrical elements, the elements each having a cylindrical configuration, the first elements being fixedly positioned in the interior surface of the coupling tube the second element being axially slidable in the interior surface of the coupling tube with a groove receiving the second element whereby when the endotracheal tube is inserted into the input end of the coupling tube it will slide the second element within the groove into contact with the first element to close the switch and a circuit.

6. A breathing circuit disconnect warning method comprising:

providing an endotracheal tube;

providing a breathing circuit supply tube with a pair of spaced electrically conductive strips; and providing a coupling tube having an output end with a normally open switch including a first electrically conductive element and a spaced second electrically conductive element, the coupling tube also having an input end with a first electrically conductive ring and a second electrically conductive ring and lines coupling the rings and the elements;

inserting the input end of the coupling tube into the supply tube to bring the rings of the coupling tube into contact with the strips of the supply tube; and inserting the endotracheal tube into the output end coupling tube whereby the switch will close and there will be an electrical connection across the switch and lines and rings and strips.

* * * * *